United States Patent
Nelson et al.

(10) Patent No.: US 11,345,423 B2
(45) Date of Patent: May 31, 2022

(54) DATA COLLECTION DEVICE WITH REMOVABLE BATTERY PACK

(71) Applicant: Ford Global Technologies, LLC, Dearborn, MI (US)

(72) Inventors: Zachary David Nelson, Dearborn, MI (US); Sudipto Aich, Dearborn, MI (US); Chih-Wei Tang, Dearborn, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 724 days.

(21) Appl. No.: 16/314,034

(22) PCT Filed: Jun. 30, 2016

(86) PCT No.: PCT/US2016/040407
§ 371 (c)(1),
(2) Date: Dec. 28, 2018

(87) PCT Pub. No.: WO2018/004601
PCT Pub. Date: Jan. 4, 2018

(65) Prior Publication Data
US 2021/0221462 A1     Jul. 22, 2021

(51) Int. Cl.
*G16H 20/30*   (2018.01)
*B62J 45/20*   (2020.01)
*B62J 45/414*  (2020.01)
*B62J 11/04*   (2020.01)
*B62J 43/30*   (2020.01)
*B62H 5/20*    (2006.01)
(Continued)

(52) U.S. Cl.
CPC ............... *B62H 5/20* (2013.01); *B62J 11/00* (2013.01); *B62J 11/04* (2020.02); *B62J 43/30* (2020.02); *B62J 45/20* (2020.02); *B62J 45/414* (2020.02); *G01C 21/3626* (2013.01); *G16H 20/30* (2018.01)

(58) Field of Classification Search
CPC .... B62H 5/20; B62J 11/00; B62J 11/04; B62J 43/30; B62J 45/20; B62J 45/40; B62J 45/414; G01C 21/26; G01C 21/3626; G16H 20/30
See application file for complete search history.

(56) References Cited

U.S. PATENT DOCUMENTS

| | | | |
|---|---|---|---|
| 5,704,803 A | * | 1/1998 | Oshima ............... H01M 50/24 439/500 |
| 2004/0189722 A1 | * | 9/2004 | Acres .................. G01C 23/00 715/866 |

(Continued)

*Primary Examiner* — Hunter B Lonsberry
*Assistant Examiner* — Daniel L Greene
(74) *Attorney, Agent, or Firm* — Brandon Hicks; Eversheds Sutherland (US) LLP

(57) ABSTRACT

An activity tracker includes a device that includes a sensor component, a radio, a housing, and a removable portion. The sensor component is configured to obtain bicycle route information based on one or more sensors. The radio is configured to wirelessly communicate the bicycle route information to a remote computing device. The housing includes at least a portion of the sensor component and the radio. The removable portion includes a battery. The removable portion and the housing, when coupled, create a watertight seal to protect electronic components of the device.

20 Claims, 12 Drawing Sheets

(51) Int. Cl.
*G01C 21/36* (2006.01)
*B62J 11/00* (2020.01)

(56) References Cited

U.S. PATENT DOCUMENTS

| | | | | |
|---|---|---|---|---|
| 2005/0195094 A1* | 9/2005 | White | .................. | G01C 3/08 |
| | | | | 340/870.01 |
| 2010/0282001 A1* | 11/2010 | Sasaki | .................. | B62K 19/34 |
| | | | | 73/862.49 |
| 2013/0061504 A1* | 3/2013 | Malherbe | .............. | F41G 11/003 |
| | | | | 42/84 |
| 2013/0150028 A1* | 6/2013 | Akins | ................... | H04W 4/021 |
| | | | | 455/427 |
| 2015/0122566 A1* | 5/2015 | Constien | .................. | B62K 5/05 |
| | | | | 180/210 |
| 2017/0240052 A1* | 8/2017 | Carmignani | ............. | B62J 99/00 |
| 2018/0334216 A1* | 11/2018 | Montez | ................... | B62J 50/22 |

* cited by examiner

DATA COLLECTION DEVICE WITH REMOVABLE BATTERY PACK

TECHNICAL FIELD

The present disclosure relates to activity tracking and more particularly relates to tracking routes and activity on a bicycle or other human powered transportation vehicle.

BACKGROUND

Human powered transportation vehicles, such as bicycles, can be pedaled or otherwise powered by human riders to provide transportation. Bicycles and other human powered transportation vehicles have been gaining popularity and provide for a significant amount of leisure, commuter, or commercial transportation. In fact, the number of bicyclists in cities is growing as a year-over-year trend. In some cases, it is useful or even necessary for bicyclists or bicycle owners to track commute or riding activities. This data may be useful for both for personal interests as well as the interests of city planners, automobile makers, etc.

Users of human powered transportation vehicles need a data collection system that is both safe and secure. At the same time, these users need a device that is discrete so as to not draw extra attention to the human powered transportation vehicle thus providing an added incentive for a would-be thief to steal the human powered transportation vehicle.

DETAILED DESCRIPTION

Figure 1:
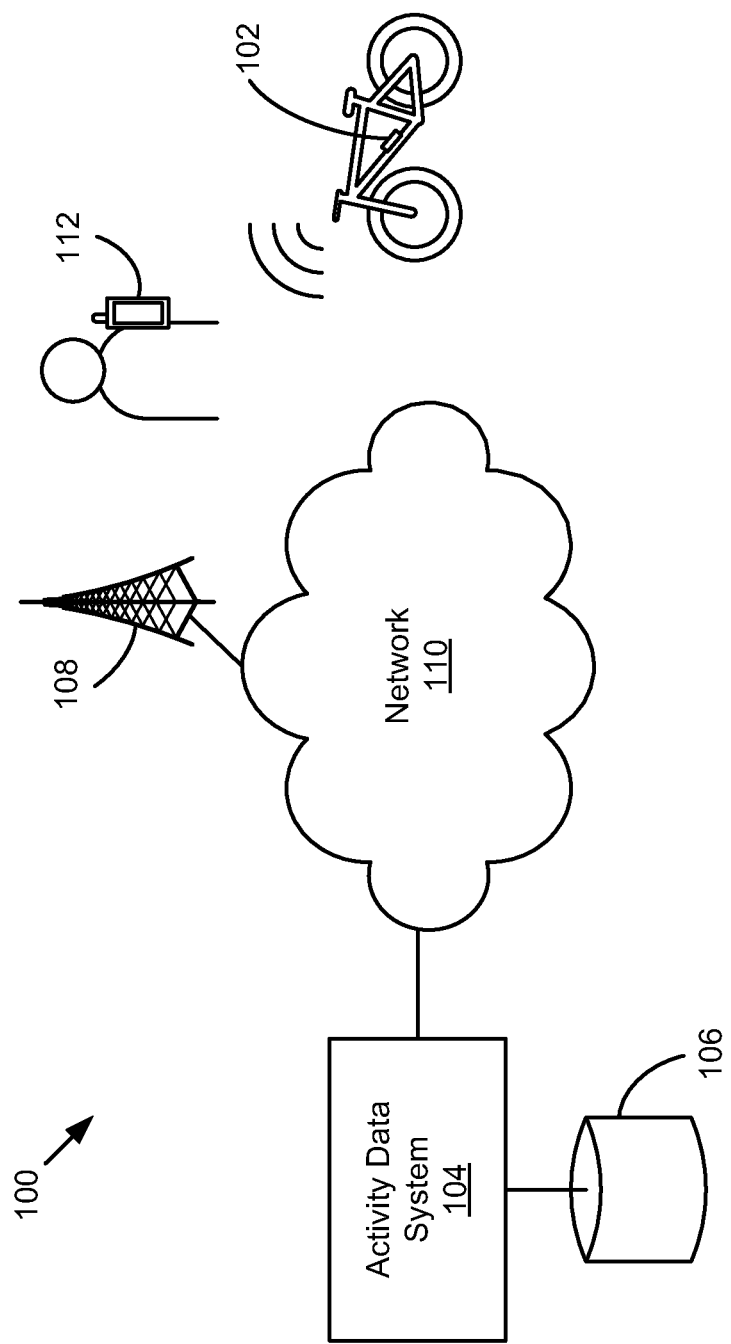
FIG. 1 is a schematic diagram illustrating an example system for collecting data for the use and routes of a human powered transportation vehicle.

Applicants have developed and herein present systems, methods, and devices for gathering information about routes or activity for bicycles or other human powered transportation vehicles. According to one embodiment, an activity tracker may be mounted or integrated into a bicycle for collecting data. The activity tracker may also be referred to herein as a data collection device. The activity tracker may enable connected bicycle applications and systems to provide highly valuable data to consumers and original equipment manufacturers (OEMs) alike. In one embodiment, the activity tracker uses a wireless connection and bicycle motion to properly connect over Bluetooth and stream data to a user's phone or directly to the cloud. In another embodiment, the activity tracker stores data locally and periodically synchronizes with another device or system using a cable or wireless interface. Because the activity tracker, or a portion of the activity tracker, may remain with a bicycle when it is locked or left in a public location, the activity tracker may have a discrete profile so as to not draw extra attention to limit providing an added incentive for a thief to steal the bicycle.

According to one embodiment, the activity tracker may be securely attached to a bicycle or other human transportation vehicle. In one embodiment, the activity tracker does not need to be removed from the bicycle for synchronization, data communication, or recharging. For example, the activity tracker may be rigidly attached to the bicycle using a water bottle cage having holes or secure zip ties anywhere on the frame. Locking bolts or secure zip ties may prevent a thief from taking or stealing the activity tracker. In one embodiment, the activity tracker includes a removable battery pack so that the device can be recharged without having to remove the activity tracker itself or a main portion of the activity tracker. The activity tracker or data collection device may have a wireless transceiver so that the data collected from the bicycle can be transmitted to a user's smart phone (e.g., via Bluetooth) or to a remote server (e.g., via a wireless mobile network such as a cellular network).

In one embodiment, the activity tracker includes a mounting member or mechanism for attaching or mounting the activity tracker to a bicycle or other human powered transportation vehicle. In one embodiment, the mounting member may be configured for attachment to a bicycle using standardized holes and hole spacing to match a water bottle holder. Many bicycles, as manufactured, use the same spacing and size for screw/bolt holes that can be used for mounting water bottle cages. In one embodiment, the design utilizes this common interface such that a data collection device can be installed on almost any bicycle. The activity tracker device can be installed with normal bolts or tamper-resistant bolts to limit chances that the device will be stolen. Alternatively or additionally, the activity tracker may include zip tie holes integrated into a chassis or housing of the activity tracker so that the activity tracker can be securely installed anywhere else on the bicycle (or other human powered transportation vehicle) in the absence of standardized water bottle cage holes. In one embodiment, a water bottle cage may be mounted on top of the activity tracker, thus allowing a cyclist or other rider to easily bring water bottles with them.

In one embodiment, the activity tracker comprises a removable battery. The activity tracker may include a removable portion that includes a rechargeable battery so that the rest of the activity tracker can remain on the bicycle (e.g., securely mounted) while the battery is recharged. Also, because the battery is removable, there may be no need to bring the bicycle (or the whole activity tracker or chassis/housing) to a location where an electrical outlet or charging port is available. For example, the bicycle and activity tracker may be able to remain in a bicycle storage location, such as a garage, shed, or the like, where no electrical power is available. The battery pack, or removable portion, may include or form an environmental seal with the housing or chassis of the activity tracker to protect from water, dirt, or other environmental conditions.

In one embodiment, the removable portion includes electrodes for providing selective electrical communication between the battery and a remaining portion of the activity tracker. Similarly, the electrodes may selectively establish electrical communication with a battery charger. In one embodiment, the electrodes may include exposed conductive surfaces, electrode posts, or the like. In one embodiment, the removable portion may include a universal serial bus (USB) port for charging the battery. In one embodiment, a USB port, charging electrodes, or the like are surrounded by an elastomer or seal material that provides an environmental seal. The housing and removable portion may include attachment or interaction mechanisms to hold the removable portion firmly attached and against the housing to maintain the seal. Similarly, the removable portion, when attached, is held firmly so that the battery does not fall off or become electrically disconnected during riding or transportation.

According to one embodiment, an activity tracker includes a pedal cadence sensor. Cyclists, including recreational and commuter cyclists, often care about pedal cadence as they ride. Pedal cadence can be useful in measuring rider performance. In one embodiment, pedal cadence may also be useful to embedded software of an activity tracker in order to detect whether or not a rider is actively riding the bicycle (e.g., versus riding on a train or transporting a bicycle). Embodiments disclosed herein may include an activity tracker that includes a pedal sensor. With the activity tracker mounted on a frame of the bicycle (e.g., using zip ties or a water bottle holder mount) the activity tracker may provide a frame-mounted pedal proximity sensor, which resides in a main body (or housing) of a data collection device or activity tracker. A light-based or magnetic based sensor embedded in the main housing of the activity tracker may be used to detect the proximity of a pedal and thereby produce (for example) an average pedal rotation speed. Pedal rotation may also useful from an internal operation perspective. For example, the activity tracker may only track/log data when it is detected that the rider is pedaling. An activity tracker with a built-in pedal proximity sensor may allow a user to omit installation/addition of a separate pedal cadence sensor. In this case, the rider needs only install the activity tracker to meet multiple needs.

The term "human powered transportation vehicle," as used herein, is given to mean any type of transportation vehicle whose movement is powered by human input. Example human powered transportation vehicles may include vehicles such as a bicycle, recumbent bicycle, tricycle, pedal powered boat, or other pedal powered vehicle. Examples of other types of human powered transportation vehicles include scooters, skateboards, or the like. Some examples provided herein are given with respect to certain types of human powered transportation devices, such as with respect to a bicycle. However, such examples are given by way of example only and it is contemplated within the scope of the present disclosure that examples given with respect to one type of human transportation device may be applied to other types of human transportation devices.

Further embodiments and examples will be discussed in relation to the figures below.

Turning to the figures, FIG. 1 is a schematic diagram illustrating a system 100 for obtaining, tracking, and/or storing route data, activity, data or any other data gathered for a bicycle or human powered transportation vehicle. The system 100 includes an activity tracker 102 device mounted on a human powered transportation vehicle. The activity tracker 102 may gather route data or any other information about the use, location, or riding of the human powered transportation vehicle. In one embodiment, the activity tracker 102 transmits the route data or other data for remote storage on an activity data system 104. The activity data system 104 may store and/or provide access to stored activity data. The activity data system 104 may store data in a database 106 or other data store. In one embodiment, the activity tracker 102 may transmit data to the activity data system 104 via communication node 108, such as a wireless access point, base station of a cellular communications network, or the like. The activity data system 104 may forward the data for storage via a network 110, such as the Internet.

In one embodiment, the activity tracker 102 may include a radio that is configured to communicate with a smart phone 112 or other portable communication device of a user. For example, the activity tracker 102 may transmit route data or other data to the smart phone 112, which may store the data or forward the data on to the activity data system 104. The smart phone 112 may include an application that is configured to receive, store, and/or access data. In one embodiment, the application may provide an interface for data visualization, route information, activity data, or other information about the riding activity of a user on one or more human powered transportation vehicles. For example, the application on the smart phone 112 may allow a user to access or view data stored locally on the smart phone 112 and/or data stored by the activity data system 104. In one embodiment, all data for a user, a plurality of users, a bicycle, or fleet of bicycles may be stored by the activity data system 104 for later access or analysis.

Figure 2:
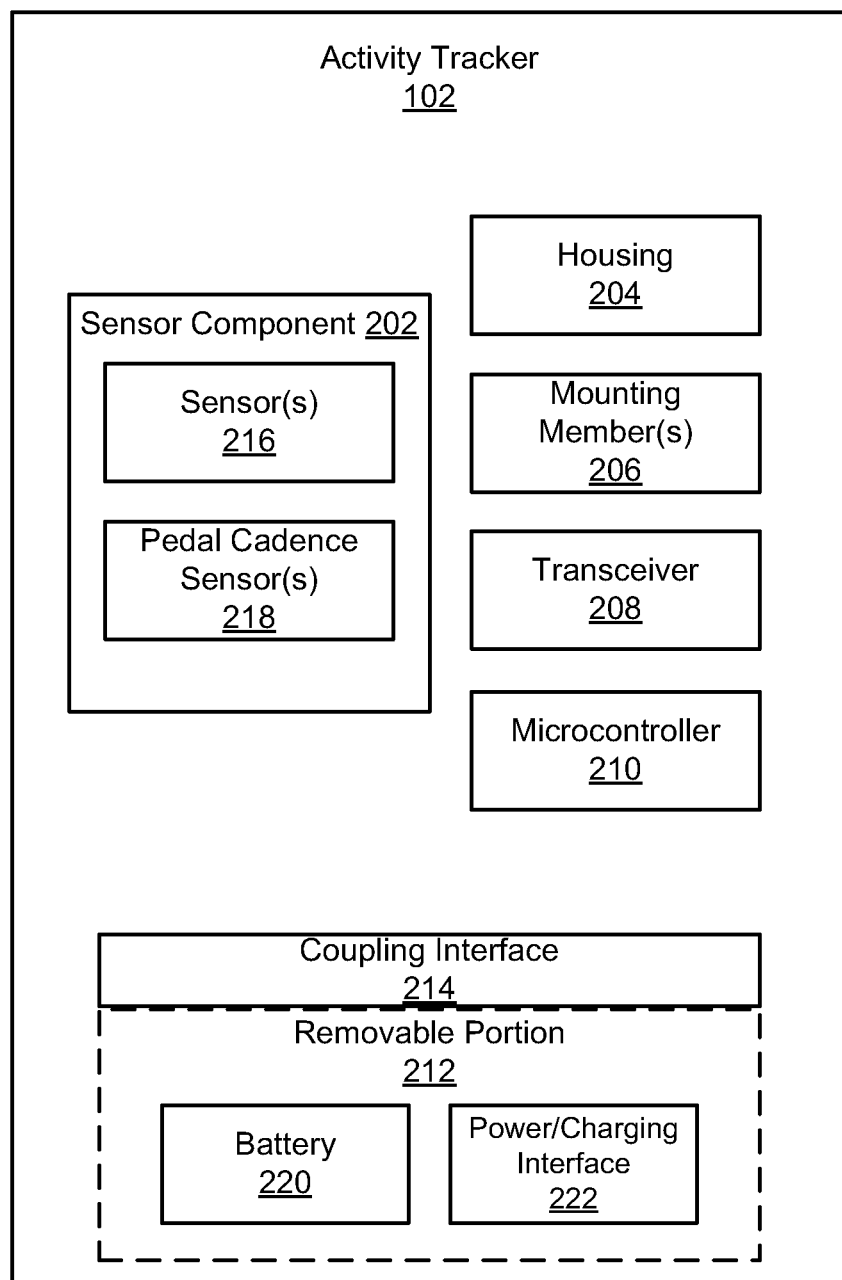
FIG. 2 is a schematic block diagram illustrating an activity tracker, according to one embodiment.

Turning to FIG. 2, a schematic block diagram is shown illustrating example components of an activity tracker 102. In the depicted embodiment, the activity tracker 102 includes a sensor component 202, a housing 204, one or more mounting members 206, a transceiver 208, a microcontroller 210, a removable portion 212, and a coupling interface 214.

The sensor component 202 obtains sensor data regarding the usage of a human powered transportation vehicle, such as a bicycle. The sensor data may include information about a route traveled by the human powered transportation vehicle, such as information about a location, path, temperature, altitude, pedal cadence, time, vibration or acceleration information, or other information gathered by one or more sensors. The sensor component 202 may store the route information or sensor data in a memory of the activity tracker 102 or sensor component 202. In one embodiment, the route information may include any type of information about the usage of a bicycle or human powered transportation vehicle on which the activity tracker 102 is mounted or with which the activity tracker 102 is traveling. For example, bicycle riders may wish to see information about distance traveled for a trip, time duration for a trip, altitude gained or lost, a map of a route, pedal cadence during riding of one or more routes, acceleration during a route, or any other information about the conditions, location, or route traveled by a rider. In one embodiment, the sensor component 202 may also detect the occurrence of events. For example, the sensor component 202 may detect events such as the presence of a rider on the human powered transportation vehicle, the beginning of a trip, the ending of a trip, or other events that occur during riding of a human powered transportation vehicle.

The sensor component 202 may include one or more sensors 216 that are used to obtain data or information about the usage or routes of a human powered transportation vehicle. In one embodiment, the sensors 216 include a positioning system receiver, such as a receiver for a global positioning system (GPS), global navigation satellite system (GLONASS), cellular network positioning system, or any other positioning system. The positioning system receiver may be used to obtain information about a geographic location of the activity tracker 102 (and thus a corresponding human transportation device) such as latitude, longitude, altitude, or the like. In one embodiment, the sensors 216 include an accelerometer for detecting acceleration events, orientation of the human powered transportation vehicle (e.g., leaning, upright, or the like), bumps, impacts, or other changes in velocity or position of the activity tracker. In one embodiment, the sensors 216 include a thermometer for detecting a current temperature at or near the activity tracker 102. In one embodiment, the sensors 216 include a compass, such as an electronic or magnetic compass, for determining a geographic orientation or heading of the activity tracker 102. In one embodiment, the sensors 216 include a barometer for detecting a current altitude, weather condition, or the like about a current location of the activity tracker 102. In one embodiment, the sensors 216 include a humidity sensor for detecting a current humidity or weather condition at a location of the activity tracker 102. The sensors 216 may be integrated as part of and/or within the sensor component 202 or activity tracker 102 for simplicity and robust operation. In one embodiment, one or more of the sensors 216 may be located separate from or external to the sensor component 202 and/or the activity tracker 102. For example, external sensors may communicate with and provide sensor data to the sensor component 202.

In one embodiment, the sensor component 202 includes a pedal cadence sensor 218. See FIG. 10 and associated discussion. According to one embodiment, the pedal cadence sensor 218 is integrated with the activity tracker 102 so that a separate device and/or mounting location are not needed to obtain information about pedal cadence. In one embodiment, the pedal cadence sensor 218 may include a light-based or magnetic based sensor that detects a pedal, or corresponding sensor or trigger portion on a pedal. Based on detected proximity, change in proximity, and/or cycle of detected peaks in proximity, the pedal cadence sensor 218 may calculate a pedal rotation speed. The sensor component 202 may use the pedal cadence data to determine an average pedal rate of a rider. Based on the pedal rate or the pedal cadence sensor 218, the sensor component 202 may be able to determine whether a rider is currently riding on the human powered transportation vehicle. In one embodiment, the sensor component 202 only obtains and/or stores sensor data when it detects that a rider is riding a bicycle or human powered transportation vehicle that the activity tracker 102 is riding with or mounted on.

The housing 204 provides a structural and/or protective cover for housing one or more components of the activity tracker 102. The housing 204 may include an exterior cover in which other components, such as the sensor component 202 and transceiver 208 are mounted or secured. The housing 204 may also provide a structural chassis on which other portions of the activity tracker 102 can be mounted, secured, or coupled to provide a rigid structural body for other components. The housing 204 may include or form one or more mounting members for securing the housing 204 and/or the activity tracker 102 to a bicycle or human powered transportation vehicle. An example housing 204 is illustrated in FIGS. 3-8.

The mounting members 206 may include mechanical shapes or features formed by a chassis, housing 204, or other portion of the activity tracker 102 for mounting or securing the activity tracker 102 to a bicycle or human powered transportation vehicle. See, for example, FIGS. 3-4 and 8. In one embodiment, a mounting member 206 may include one or more holes or slots passing through a housing 204 or chassis of the activity tracker 102. The holes or slots may be spaced to match a bottle cage mounting location on a bicycle. For example, bicycles may include a standardized spacing, hole size, and locations for bolt holes for mounting hardware or accessories, such as a bottle cage, a holder for a pump, or the like. In embodiments where the mounting members 206 include holes or slots with a spacing to match standardized mounts, the activity tracker 102 may be easily and securely mounted to bicycles or human powered transportation vehicles with matching mounting locations. In one embodiment, a mounting member 206 may include one or more holes, slots, or grooves for receiving a zip tie for attachment to a frame of the bicycle or human powered transportation vehicle. The mounting members 206 may be integrated within the housing 204 or chassis of the activity tracker 102. Using locking or anti-tamper bolts or zip ties, the activity tracker 102 may be mounted to a bicycle or human powered transportation vehicle in a way that limits or prevents theft or unauthorized removal of the activity tracker 102.

The transceiver 208 is configured to provide wired or wireless communication between the activity tracker 102 and another computing or communication device. In one embodiment, the transceiver 208 includes a radio which may be used to communicate route data or sensor data to another device. For example, the transceiver 208 may include a radio for communicating over a cellular, wide area, or other mobile network (such as a 3GPP, WiMax, or other wireless network). In one embodiment, the transceiver 208 may be used for synchronizing or uploaded route data, sensor data, or other data gathered by the sensor component 202 for storage and/or access at a cloud location or remote storage. As another example, the transceiver 208 may include a radio for communicating with a nearby device, such as a Bluetooth, Zigbee, or other short distance communication standard. In one embodiment, the transceiver 208 is configured to communicate route data, sensor data, or other data gathered by the sensor component 202 to a smart phone or other computing device traveling with the activity tracker 102 (or a human powered transportation device with which the activity tracker 102 is traveling). The smart phone or other device may then store the data locally and/or forward the data to a remote or cloud location for storage and later access.

The microcontroller 210 may include a processor for controlling operation of the activity tracker 102. For example, the microcontroller 210 may perform processing, data storage, data access, or other functions for any of the other components of the activity tracker 102. In one embodiment, the microcontroller 210 may include a low power processor for coordinating, triggering, or performing operations on behalf of or based on the components of the activity tracker 102.

The removable portion 212 includes a portion of the activity tracker 102 that is removable from a housing 204 or chassis of the activity tracker 102. See, for example, FIGS. 3-7. For example, the removable portion 212 may be selectively coupled or decoupled from the activity tracker 102 at a coupling interface 214. The removable portion 212 may include a battery 220 and a power/charging interface 222. The battery 220 may include a rechargeable battery or battery pack. The power/charging interface 222 may include contacts or electrode posts for providing electrical communication with the battery 220. For example, the power/charging interface 222 may interact or contact electrical surfaces or contacts on the coupling interface 214, when coupled, to power the sensor component 202, transceiver 208, microcontroller 210, and/or other components of the activity tracker 102. The power/charging interface 222 may include a physical port or contact for charging the battery 220. In one embodiment, the power/charging interface 222 includes a USB interface. In one embodiment, the power/charging interface 222 includes a wireless charging interface such as a wireless charging coil. In one embodiment, the power/charging interface 222 may include a single interface (e.g., set of contacts) for both providing power to the sensor component 202 and receiving power for charging the battery 220. In one embodiment, the power/charging interface 222 may include two interfaces (e.g., two sets of contacts): one for providing power to the sensor component 202; and another for receiving power for charging the battery 220.

The coupling interface 214 comprises physical mechanisms and/or features for securing the removable portion 212 to the rest of the activity tracker 102. See FIGS. 5-7, which illustrate an example coupling interface 214 between a removable portion 212 and a housing 204 of an activity tracker 102. In one embodiment, the coupling interface 214 allows the removable portion 212 to be removable from the activity tracker 102 and/or the housing 204 when the housing 204 is mounted to the bicycle. For example, the mounting member 206 may not be located on the removable portion 212 so that any bolt, zip ties, or other fasteners or mechanisms used to attach the activity tracker to a bicycle or human powered transportation vehicle do not interfere with removal of the removable portion 212.

The coupling interface 214 may provide a watertight or waterproof seal for protecting electronic or electrical components of the activity tracker 102 from water, humidity, dirt, or other environmental conditions. For example, the coupling interface 214 may provide a watertight seal that protects the power/charging interface 222 from water or rain. The coupling interface 214 or the removable portion 212 may include an elastomer material that, when coupled, are pressed together to form a water tight seal around a region where the power/charging interface 222 and/or other electrical components of the removable portion 212 or coupling interface 214 are located. In one embodiment, the coupling interface 214 provides a water tight seal around electrical connectors for providing electrical communication between the removable portion 212 and components in the housing 204. In one embodiment, the coupling interface 214 provides a water tight seal around a charging port on the removable portion 212 for charging the battery 220.

The components 202-222 are given by way of illustration only and may not all be included in all embodiments. In fact, some embodiments may include only one or any combination of two or more of the components 202-222. Furthermore, some of the components 202-222 may be located outside the activity tracker 102, such as within separate devices or sensors that are in communication with the activity tracker.

Figure 3:
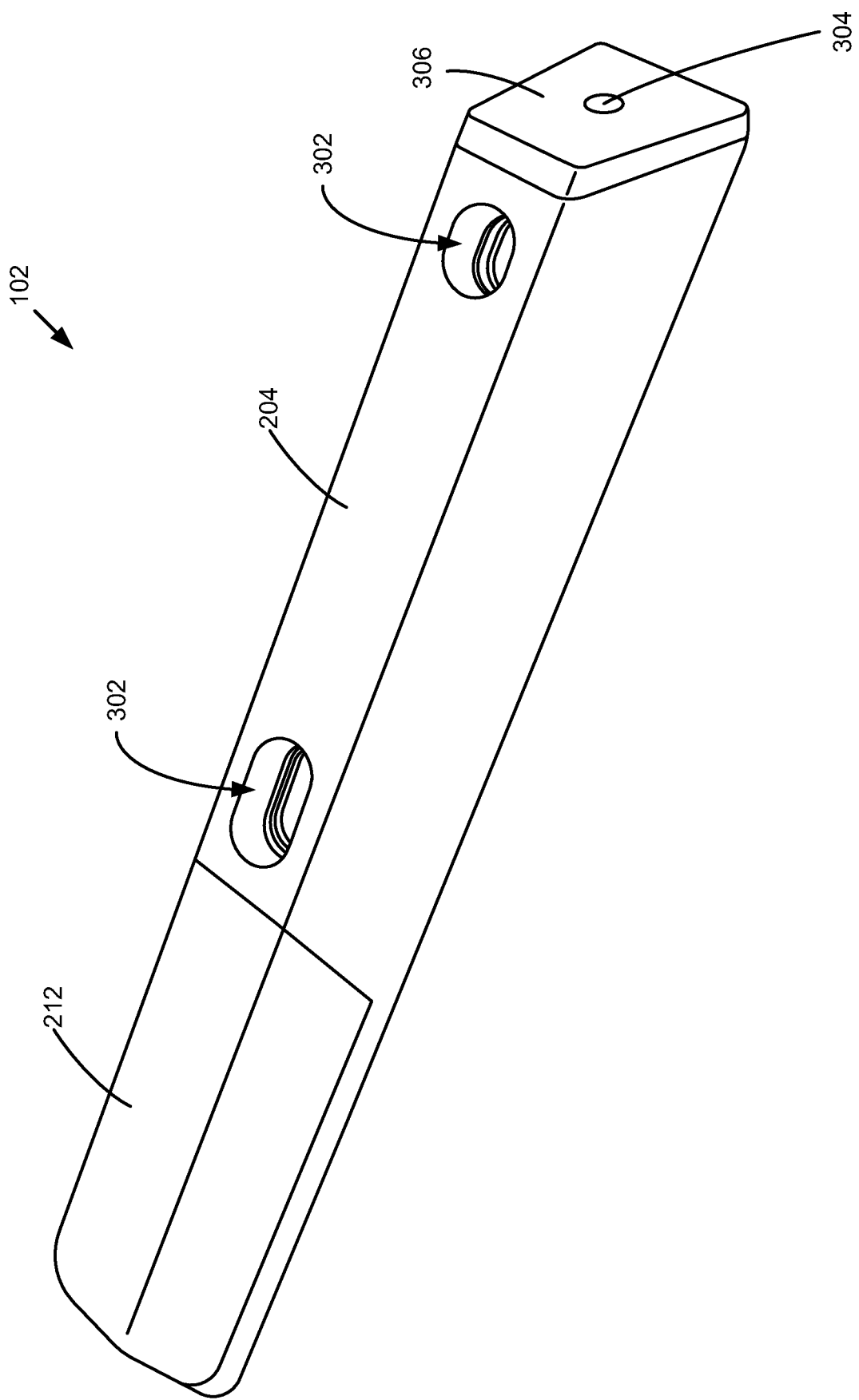
FIG. 3 is a perspective top view of an activity tracker, according to one embodiment.

Turning now to FIGS. 3-11, example embodiments of an appearance and configuration of an activity tracker 102 are provided. FIG. 3 is a perspective top view of an activity tracker 102. The activity tracker 102 comprises an elongated housing 204 with mounting members that form holes 302 for fastening/mounting the activity tracker 102 to an accessory mount of a bicycle or other human powered transportation vehicle. In one embodiment, the holes 302 may form a slotted or un-slotted counter sunk M5 screw boss for tolerance. For example, a slotted hole or boss may allow for accommodations in slight differences in distances between mounting locations for screws. A removable portion 212 is shown in an attached configuration to the housing 204. The activity tracker 102 also includes a power/control button 304 and a LED indicator area 306. The power/control button 304 may be used to power the activity tracker 102 on or off, trigger pairing with another device, trigger sensor data tracking, or the like. The LED indicator area 306 may provide a region where LED indicators may light up to indicate a current status of the activity tracker 102. Example statuses may include, powered on, powered off, paired, battery low, or the like.

Figure 4:
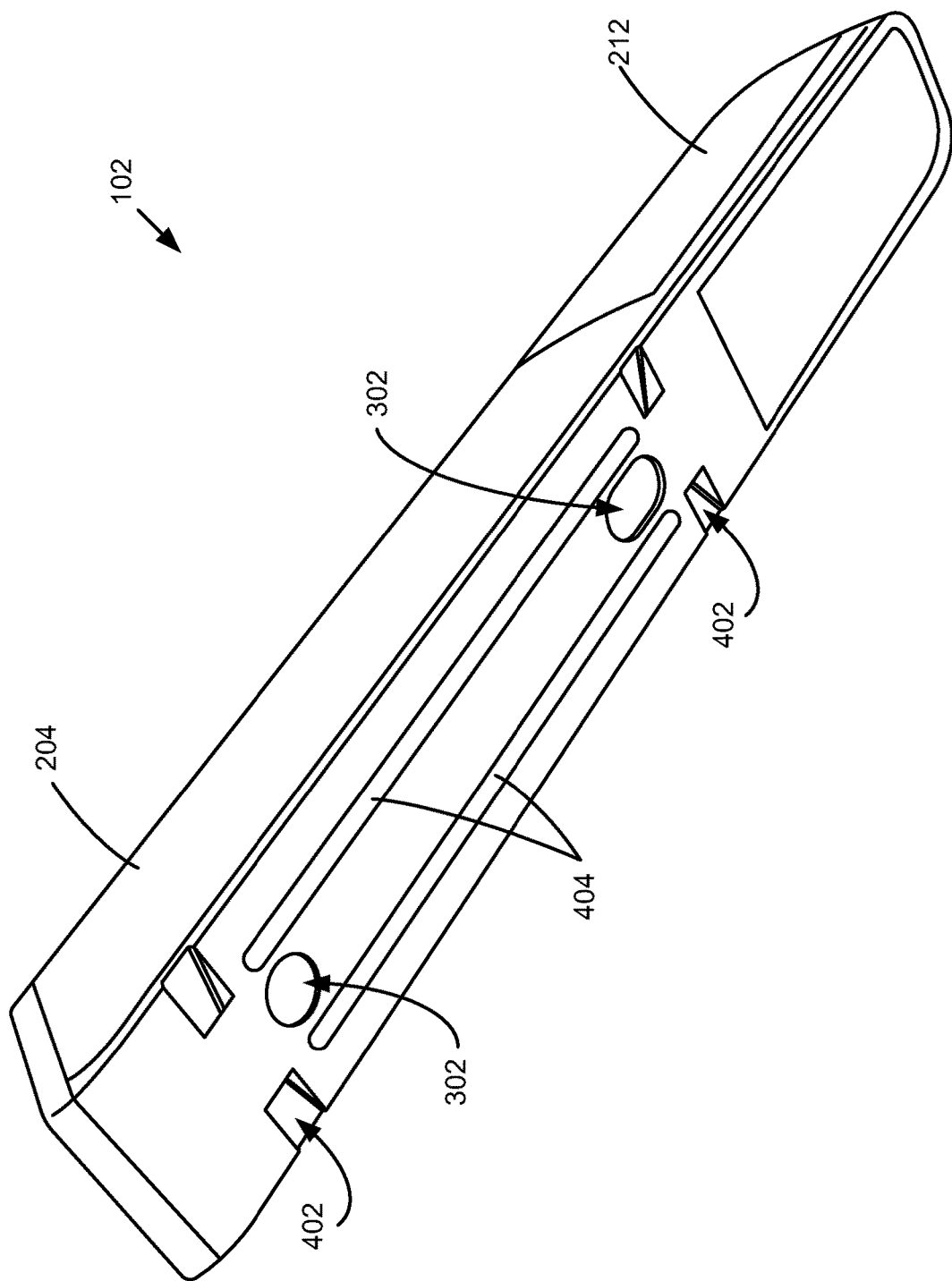
FIG. 4 is a perspective bottom view of an activity tracker, according to one embodiment.

FIG. 4 is a perspective bottom view of an activity tracker 102. The bottom end of the holes 302 is shown. Additionally, the activity tracker 102 also includes zip tie holes 402, which pass through a portion of the bottom of the housing 204. The zip tie holes 402 may allow a zip tie to pass through the zip tie holes 402 and around a frame or bar member of a bicycle or human powered transportation vehicle to secure the activity tracker 102. For example, if no water bottle mounts are available, the zip tie holes 402 may be used. The activity tracker 102 also includes elastomer ridges 404. The elastomer ridges 404 act as a rubber protector for the paint or a surface of a bicycle frame or frame of a human powered transportation vehicle. In one embodiment, the elastomer ridges 402 are part of an internal seal of the activity tracker 102 to mitigate water and dust intrusion.

Figure 5:
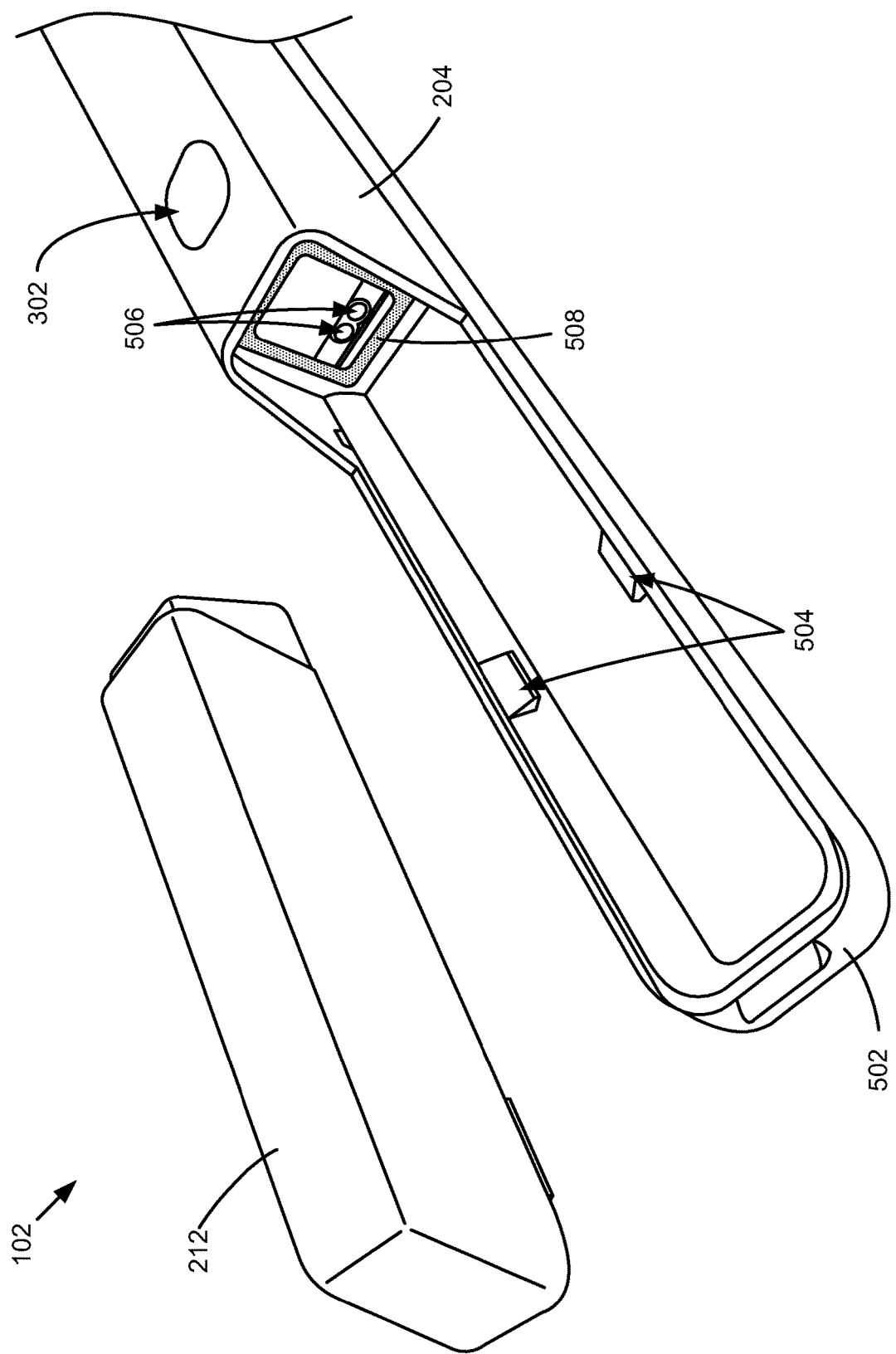
FIG. 5 is a perspective view of an activity tracker with a removable portion removed, according to one embodiment.

FIG. 5 is a perspective view of the activity tracker 102 with the removable portion 212 removed so that it is not coupled to the housing 204. A coupling member 502 is shown that extends from the housing 204 and includes locking members 504 for engaging and locking the removable portion 212 to the housing 204. A coupling interface on the housing portion is also shown. The coupling interface includes electrical contacts 506 for connecting with a battery or other electronic component in the removable portion 212. In one embodiment, the electrical contacts 506 include pads configured to contact terminals or posts on the removable portion 212. For example, the electrical contacts 506 may include spring loaded pins or pads (such as Pogo terminals). Alternatively or additionally, a USB port or interface may be included for connecting to a corresponding USB port on the removable portion 212. The electrical contacts 506, and/or other electrical or communication ports on the housing 204, may be surrounded by a sealing material 508. The sealing material 508 may include an elastomer or other material that forms a water tight seal with the removable portion to protect the electrical contacts 506 from water or environmental conditions.

Figure 6:
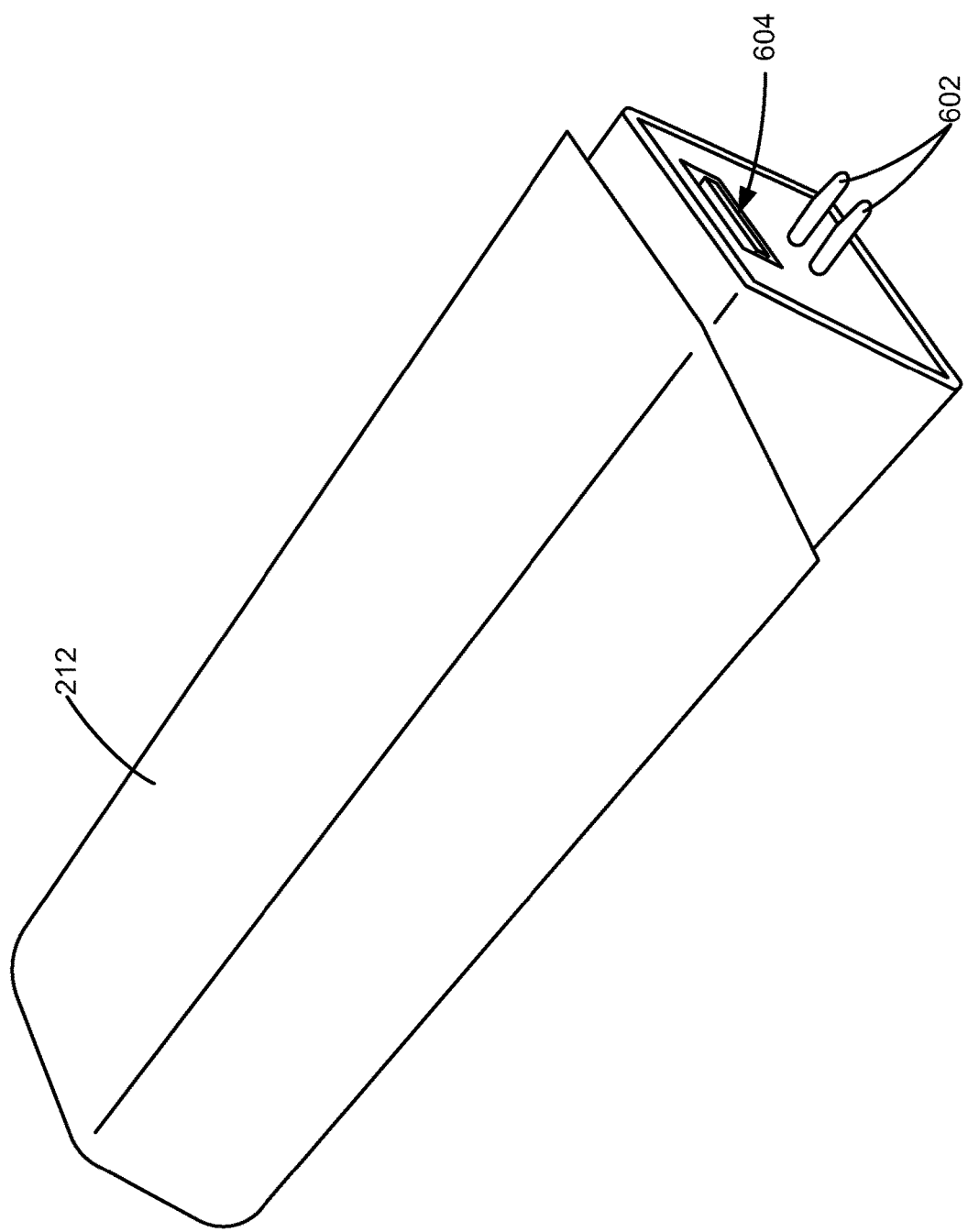
FIG. 6 is a perspective view of a removable portion removed, according to one embodiment.

FIG. 6 is a perspective view of a removable portion 212. The removable portion 212 is shown in an uncoupled configuration where the removable portion is removed from a housing 204 or remaining portion of an activity tracker 102. The removable portion 212 includes terminals 602 in electrical communication with a battery within the removable portion 212. The terminals 602 may be sized and position to contact electrical contacts on a housing 204 (such as the electrical contacts 506 shown in FIG. 5). The terminals 602 may include spring loaded terminals (such as PoGo terminals). The terminals 602 may be used to provide power to components housed within a housing 204. The terminals 602 may be used to receive power from a power source, such as a battery charger, to replenish electrical energy within a battery. In one embodiment, the removable portion 212 includes a USB port 604. The USB port 604 may also provide electrical communication with the battery so that charging of the battery may be performed using a USB cable or port on a computing device or charging device. In one embodiment, the removable portion 212 comprises a ridge or other physical portion corresponding to a seal on the housing 204 to provide a water tight seal to protect the terminals 602 and/or the USB port 604.

Figure 7A:
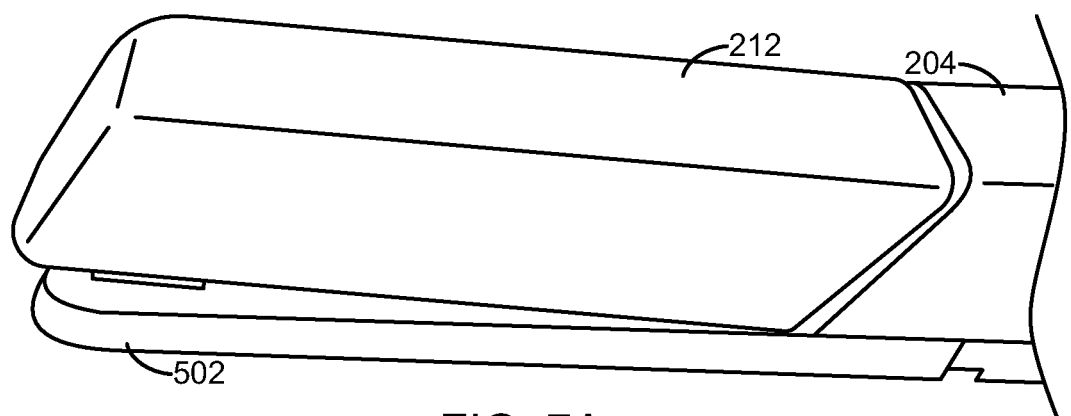
FIGS. 7A-7C illustrate views during coupling of a removable portion with a housing of an activity tracker, according to one embodiment.
Figure 7B:
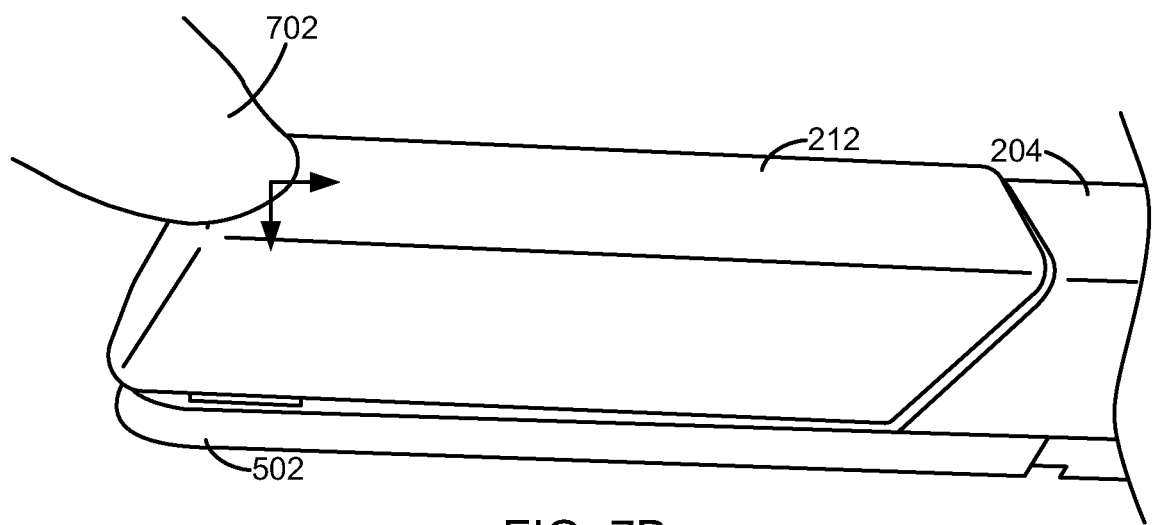
Figure 7C:
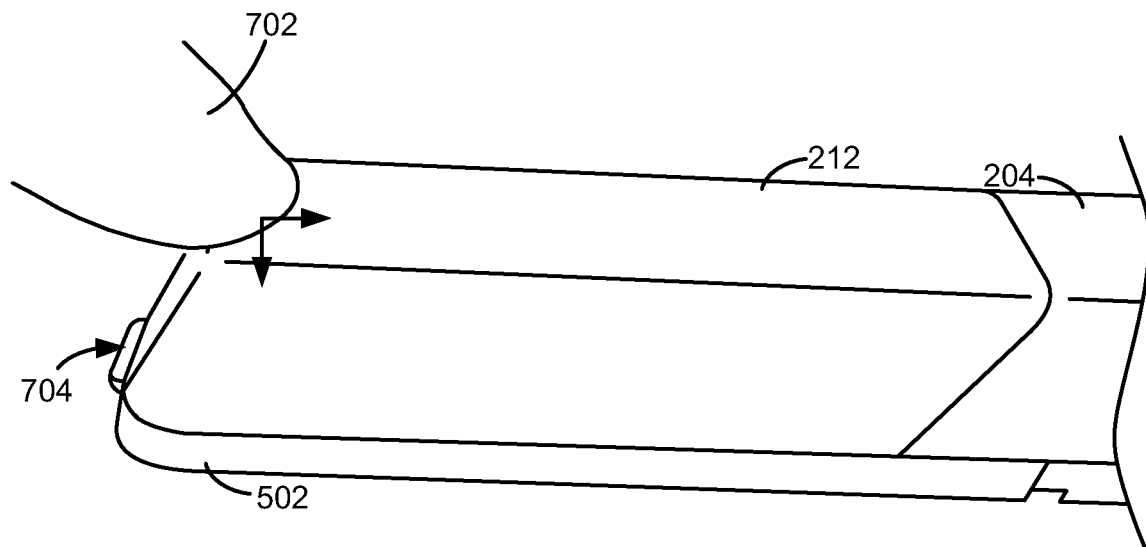

FIGS. 7A-7C illustrate coupling of a removable portion 212 with the housing 204, according to one embodiment. FIG. 7A illustrates the removable portion 212 in an uncoupled state, but is resting on the coupling member 502. FIG. 7B illustrates a user, using a finger 702 to press the removable portion 212 down and toward the housing. In FIG. 7C, the removable portion 212 is in a coupled state and locked in place by the coupling member 502. To remove a user may place their finger 702 under an edge of the removable portion (for example, at the location indicated at 704) and pry upward to unlock the removable portion from the coupling member 502. These FIGS. show the attachment mechanism for the battery pack (or removable portion). As the removable portion is installed into the main housing, it is forced forward thus pressing against the seal (see FIG. 5). The applied force around the seal may help ensure protection against water intrusion.

Figure 8:
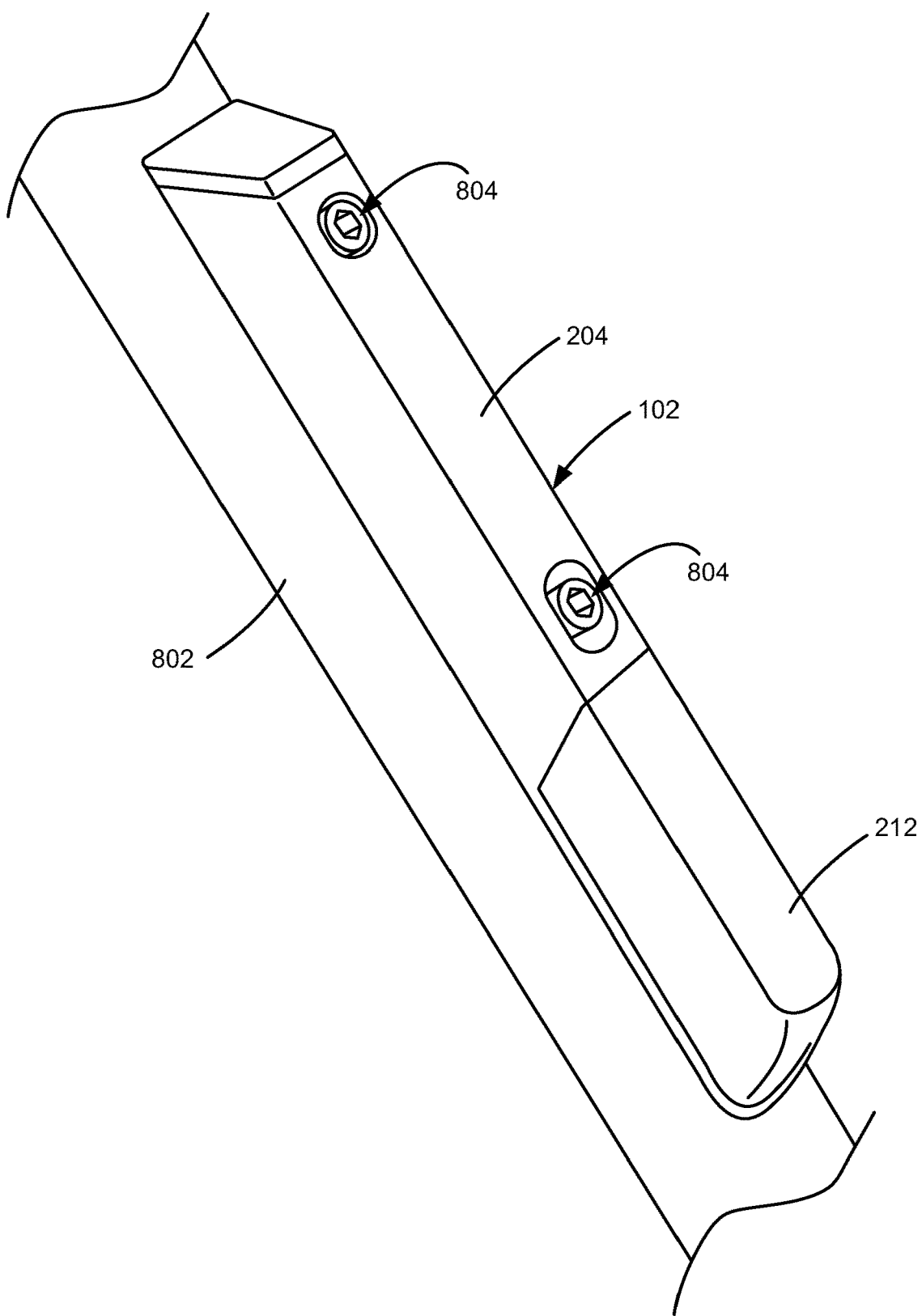
FIG. 8 is a perspective view of an activity tracker mounted on a bicycle frame, according to one embodiment.

FIG. 8 is a perspective diagram illustrating an activity tracker 102 mounted on a frame 802 of a human powered transportation vehicle. Bolts 804 are shown securing the housing 204 to the frame 802. The removable portion 212 is removable because the bolts do not pass through the removable portion 212. In one embodiment, the bolts 804 may include tamper resistant bolts so that the housing 204 remains attached and limits an unauthorized user from removing the housing 204. The removable portion 212 may be removed from the housing 204 and frame 802 to allow a battery to be recharged.

Figure 9:
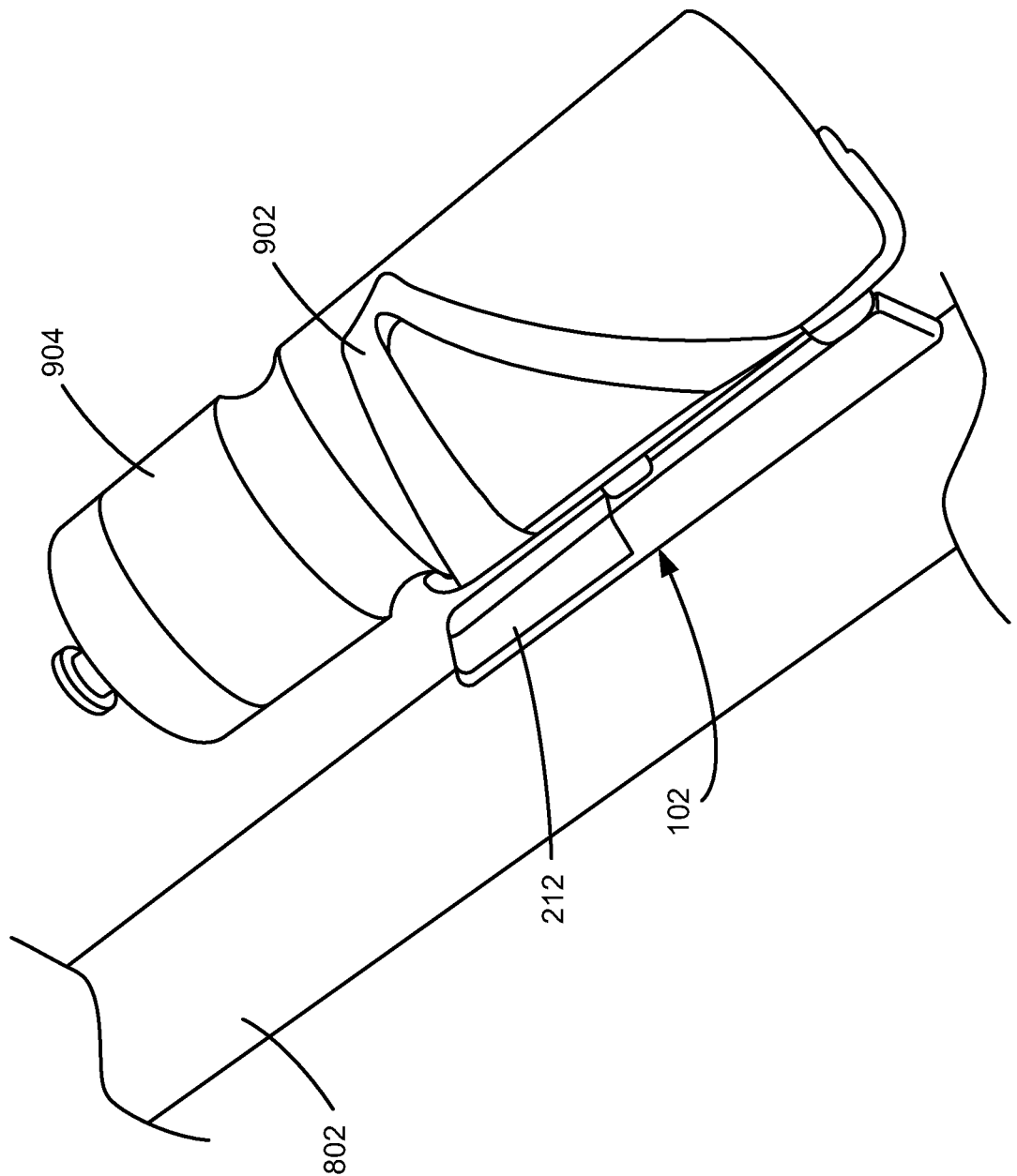
FIG. 9 is a perspective side view of an activity tracker and water bottle cage mounted on a bicycle frame, according to one embodiment.

FIG. 9 is a perspective diagram illustrating a stacked configuration for an activity tracker 102 and water bottle cage 902 on a frame 802. For example, elongated bolts that pass through both the water bottle cage 902 (or other accessory) and the activity tracker 102 may be used to secure both the water bottle cage 902 and the activity tracker 102 to the frame 802 at the same mounting location. The water bottle cage 902 holds a water bottle 904 for use by a rider. Thus, the activity tracker 102 may be used without any loss of mounting locations for use by other accessories. A removable portion 212 may still be removable even with the activity tracker 102 and/or the water bottle cage 902 mounted on the frame 802.

Figure 10:
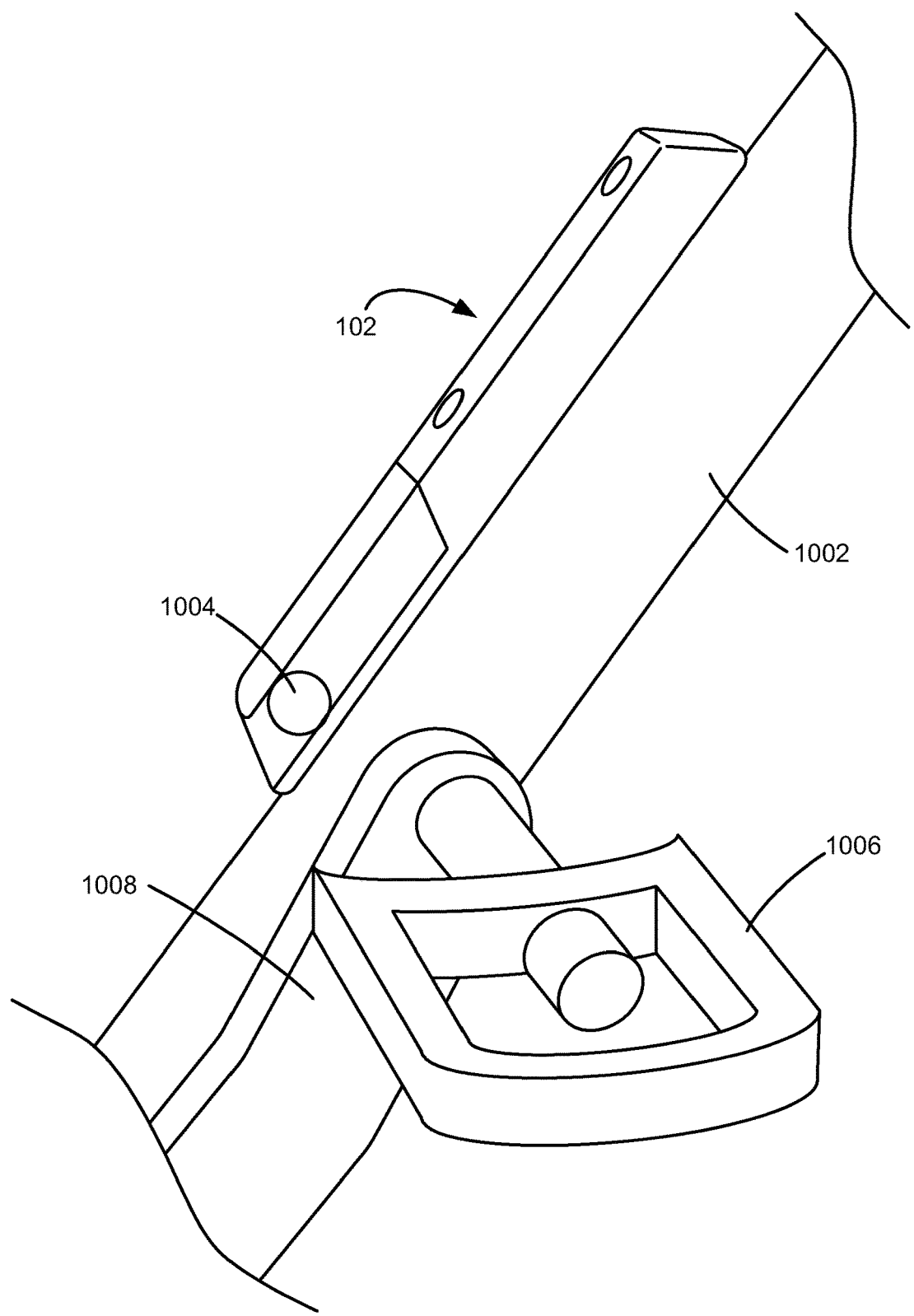
FIG. 10 is a perspective side view of an activity tracker with integrated pedal cadence sensor mounted on a bicycle frame, according to one embodiment.

FIG. 10 is a perspective side view of an activity tracker 102 mounted on a frame 1002 of a human powered transportation vehicle, such as a bicycle. The activity tracker 102 includes an integrated pedal cadence sensor 1004 (which may or may not be visible externally to the activity tracker 102). The pedal cadence sensor 1004 may detect the proximity of a pedal 1006 or pedal crank arm 1008 using a light-based or magnetic-based sensor. For example, a sensor trigger may be positioned on the pedal 1006 or pedal crank arm 1008 to activate the pedal cadence sensor 1004. For example, the sensor trigger may include a magnet, a colored sticker or paint, or other material or item that can be detected by the pedal cadence sensor 1004. In one embodiment, the position of the pedal cadence sensor 1004 on or in the activity tracker 102 is configured to position the pedal cadence sensor 1004 laterally from a pedal 1006 or pedal crank arm 1008 of a bicycle. For example, accessory mounts (such as water bottle mounts) are often positioned on a vertical or angled down tube extending between a sprocket shaft and a seat post or the handle bars of a bicycle. The position of the pedal cadence sensor 1004 with respect to holes with mounting members may be configured to place the pedal cadence sensor 1004 at a location close enough (e.g., horizontally near) to the pedal 1006 or pedal crank arm 1008 to sense a magnet or other sensor trigger.

Figure 11:
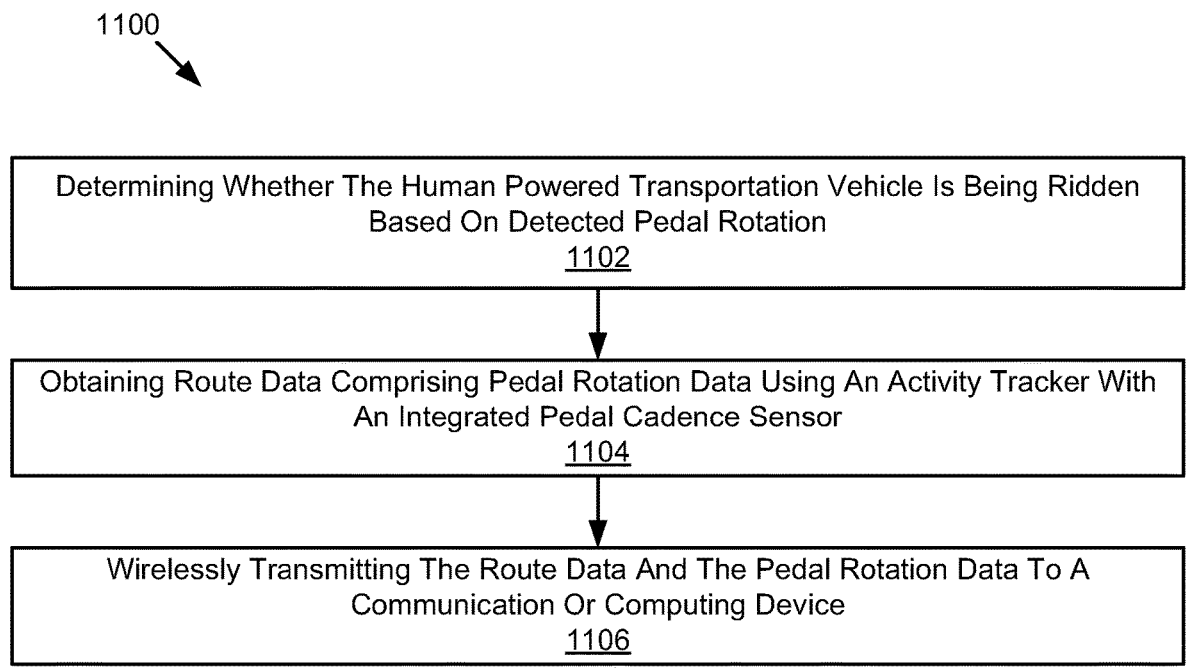
FIG. 11 is a schematic flow chart diagram illustrating a method for obtaining route information including pedal cadence information, according to one embodiment.

FIG. 11 is a schematic flow chart diagram of a method 1100 for activity tracking for a human powered transportation vehicle. The method 1100 includes determining at 1102 whether the human powered transportation vehicle is being ridden based on detected pedal rotation. The method 110 further includes obtaining at 1104, in response to determining that the human powered transportation vehicle is being ridden, route data comprising pedal rotation data using an activity tracker with an integrated pedal cadence sensor, such as pedal cadence sensor 1004. The method 1100 also includes wirelessly transmitting at 1106 the route data and the pedal rotation data to a communication or computing device.

Figure 12:
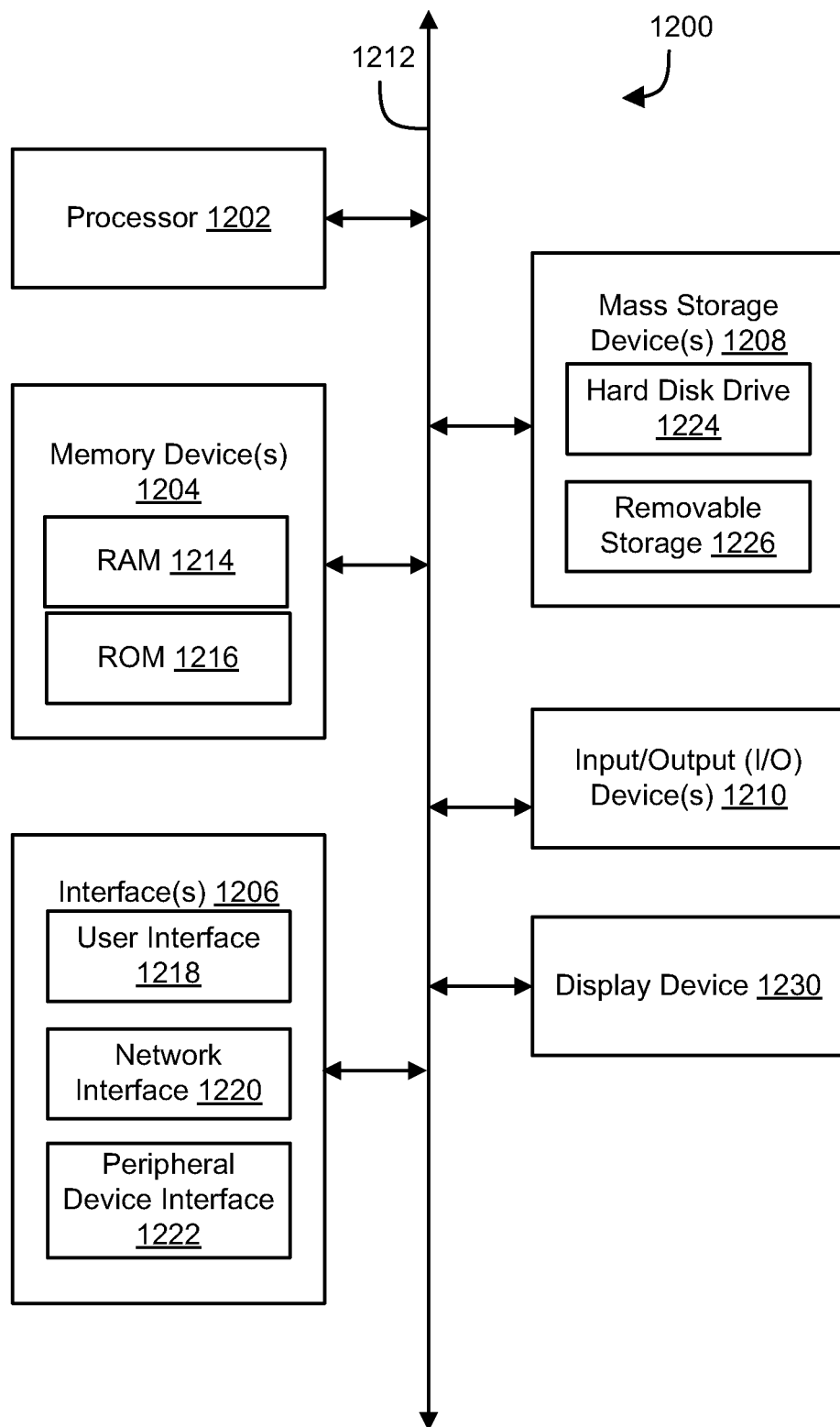
FIG. 12 is a block diagram illustrating an example computing device in accordance with the teachings and principles of the disclosure.

Referring now to FIG. 12, a block diagram of an example computing device 1200 is illustrated. Computing device 1200 may be used to perform various procedures, such as those discussed herein. Computing device 1200 can function as an activity tracker, server, a client, or any other computing entity. Computing device 1200 can perform various monitoring functions as discussed herein, and can execute one or more application programs, such as the application programs or functionality described herein. Computing device 1200 can be any of a wide variety of computing devices, such as a desktop computer, a notebook computer, a server computer, a handheld computer, tablet computer and the like.

Computing device 1200 includes one or more processor(s) 1202, one or more memory device(s) 1204, one or more interface(s) 1206, one or more mass storage device(s) 1208, one or more Input/Output (I/O) device(s) 1210, and a display device 1230 all of which are coupled to a bus 1212. Processor(s) 1202 include one or more processors or controllers that execute instructions stored in memory device(s) 1204 and/or mass storage device(s) 1208. Processor(s) 1202 may also include various types of computer-readable media, such as cache memory.

Memory device(s) 1204 include various computer-readable media, such as volatile memory (e.g., random access memory (RAM) 1214) and/or nonvolatile memory (e.g., read-only memory (ROM) 1216). Memory device(s) 1204 may also include rewritable ROM, such as Flash memory.

Mass storage device(s) 1208 include various computer readable media, such as magnetic tapes, magnetic disks, optical disks, solid-state memory (e.g., Flash memory), and so forth. As shown in FIG. 12, a particular mass storage device is a hard disk drive 1224. Various drives may also be included in mass storage device(s) 1208 to enable reading from and/or writing to the various computer readable media. Mass storage device(s) 1208 include removable media 1226 and/or non-removable media.

I/O device(s) 1210 include various devices that allow data and/or other information to be input to or retrieved from computing device 1200. Example I/O device(s) 1210 include cursor control devices, keyboards, keypads, microphones, monitors or other display devices, speakers, printers, network interface cards, modems, and the like.

Display device 1230 includes any type of device capable of displaying information to one or more users of computing device 1200. Examples of display device 1230 include a monitor, display terminal, video projection device, and the like.

Interface(s) 1206 include various interfaces that allow computing device 1200 to interact with other systems, devices, or computing environments. Example interface(s) 1206 may include any number of different network interfaces 1220, such as interfaces to local area networks (LANs), wide area networks (WANs), wireless networks, and the Internet. Other interface(s) include user interface 1218 and peripheral device interface 1222. The interface(s) 1206 may also include one or more user interface elements 1218. The interface(s) 1206 may also include one or more peripheral interfaces such as interfaces for printers, pointing devices (mice, track pad, or any suitable user interface now known to those of ordinary skill in the field, or later discovered), keyboards, and the like.

Bus 1212 allows processor(s) 1202, memory device(s) 1204, interface(s) 1206, mass storage device(s) 1208, and I/O device(s) 1210 to communicate with one another, as well as other devices or components coupled to bus 1212. Bus 1212 represents one or more of several types of bus structures, such as a system bus, PCI bus, IEEE bus, USB bus, and so forth.

For purposes of illustration, programs and other executable program components are shown herein as discrete blocks, although it is understood that such programs and components may reside at various times in different storage components of computing device 1200, and are executed by processor(s) 1202. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

Examples

The following examples pertain to further embodiments.

Example 1 is a device that includes a sensor component, a radio, a housing, and a removable portion. The sensor component is configured to obtain bicycle route information based on one or more sensors. The radio is configured to wirelessly communicate the bicycle route information to a remote computing device. The housing includes at least a portion of the sensor component and the radio. The removable portion includes a battery. The removable portion and the housing, when coupled, create a watertight seal to protect electronic components of the device.

In Example 2, the housing in Example 1 includes a mounting member for mounting the housing to a bicycle.

In Example 3, the removable portion in Example 2 is removable from the housing when the housing is mounted to the bicycle.

In Example 4, the mounting member in any of Examples 2-3 includes one or more holes or slots passing through the housing and wherein the one or more holes or slots are spaced to match a bottle cage mounting location on a bicycle.

In Example 5, the mounting member in any of Examples 2-4 includes one or more holes, slots, or grooves for receiving a zip tie for attachment to a frame of the bicycle.

In Example 6, the watertight seal in any of Examples 1-5 protects one or more of: electrical connectors for providing electrical communication between the removable portion and the housing; and a charging port on the removable portion for charging the battery.

In Example 7, the watertight seal in any of Examples 1-6 is formed between the housing and the removable portion at least in part by an elastomer material on one or more of the housing and the removable portion.

In Example 8, the device in any of Examples 1-7 further includes one or more of a microcontroller, a positioning system receiver, an accelerometer, a thermometer, a compass, and a barometer.

In Example 9, the radio in any of Examples 1-8 is configured to communicate the bicycle route information to a remote computing device comprising a portable computing device traveling with the bicycle.

In Example 10, the radio in any of Examples 1-9 is configured to communicate the bicycle route information to a remote computing device via a portable computing device traveling with the bicycle. The portable computing device communicates the bicycle route information to a server or computing device over a wireless network.

Example 11 is a human powered transportation vehicle that includes an activity tracker. The activity tracker may be attached to or integrated with the human powered transportation vehicle. The activity tracker includes a sensor component, a radio, a housing, and a removable portion. The sensor component is configured to obtain route information for the human powered transportation vehicle. The radio is configured to wirelessly communicate the route information to a remote computing device. The housing includes or houses at least a portion of the sensor component and the radio. The removable portion includes a battery. The removable portion and the housing, when coupled, create a watertight seal to protect electronic components of the activity tracker.

In Example 12, the housing in Example 11 includes a mounting member for securing the housing to the human powered transportation vehicle.

In Example 13, the removable portion in Example 12 is removable from the housing when the housing is mounted to the human powered transportation vehicle.

In Example 14, the mounting member in any of Examples 12-13 includes one or more holes or slots passing through the housing and wherein the one or more holes or slots are spaced to match one or more screw holes on a frame or other portion of the human powered transportation vehicle.

In Example 15, the mounting member in any of Examples 12-14 includes one or more holes, slots, or grooves for receiving a zip tie for attachment to a frame or other portion of the human powered transportation vehicle.

In Example 16, the watertight seal in any of Examples 11-15 protects one or more of: electrical connectors for providing electrical communication between the removable portion and the housing; and a charging port on the removable portion for charging the battery.

In Example 17, the watertight seal in any of Examples 11-16 is formed between the housing and the removable portion at least in part by an elastomer material on one or more of the housing and the removable portion.

In Example 18, the sensor component in any of Examples 11-17 includes one or more of a microcontroller, a positioning system receiver, an accelerometer, a thermometer, a compass, and a barometer.

In Example 19, the radio in any of Examples 11-18 is configured to communicate the route information to a remote computing device comprising a portable computing device traveling with the human powered transportation vehicle.

In Example 20, the radio in any of Examples 11-19 is configured to communicate the human powered transportation vehicle route information to a remote computing device via a portable computing device traveling with the human powered transportation vehicle. The portable computing device communicates the human powered transportation vehicle route information to a server or computing device over a wireless network.

Example 21 is a system or device that includes means for implementing a method, system, or device as in any of Examples 1-20.

In the above disclosure, reference has been made to the accompanying drawings, which form a part hereof, and in which is shown by way of illustration specific implementations in which the disclosure may be practiced. It is understood that other implementations may be utilized and structural changes may be made without departing from the scope of the present disclosure. References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

As used herein, "autonomous vehicle" may be a vehicle that acts or operates completely independent of a human driver; or may be a vehicle that acts or operates independent of a human driver in some instances while in other instances a human driver may be able to operate the vehicle; or may be a vehicle that is predominantly operated by a human driver, but with the assistance of an automated driving/assistance system.

Implementations of the systems, devices, and methods disclosed herein may comprise or utilize a special purpose or general-purpose computer including computer hardware, such as, for example, one or more processors and system memory, as discussed herein. Implementations within the scope of the present disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions are computer storage media (devices). Computer-readable media that carry computer-executable instructions are transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links, which can be used to carry desired program code means in the form of computer-executable instructions or data structures and which can be accessed by a general purpose or special purpose computer. Combinations of the above should also be included within the scope of computer-readable media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the disclosure may be practiced in network computing environments with many types of computer system configurations, including, an in-dash vehicle computer, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms are used throughout the description and claims to refer to particular system components. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors, and may include hardware logic/electrical circuitry controlled by the computer code. These example devices are provided herein purposes of illustration, and are not intended to be limiting. Embodiments of the present disclosure may be implemented in further types of devices, as would be known to persons skilled in the relevant art(s).

At least some embodiments of the disclosure have been directed to computer program products comprising such logic (e.g., in the form of software) stored on any computer useable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the disclosure. Thus, the breadth and scope of the present disclosure should not be limited by any of the above-described exemplary embodiments, but should be defined only in accordance with the following claims and their equivalents. The foregoing description has been presented for the purposes of illustration and description. It is not intended to be exhaustive or to limit the disclosure to the precise form disclosed. Many modifications and variations are possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the claims appended hereto, any future claims submitted here and in different applications, and their equivalents.

What is claimed is:

1. A device comprising:
   a sensor component configured to obtain bicycle route information based on one or more sensors;
   a radio configured to wirelessly communicate the bicycle route information to a remote computing device;
   a housing comprising at least a portion of the sensor component and the radio; and
   a removable portion comprising a battery, wherein the removable portion and the housing, when coupled, create a watertight seal between the removable portion and the housing to protect electronic components of the device.

2. The device of claim 1, wherein the housing comprises a mounting member for mounting the housing to a bicycle.

3. The device of claim 2, wherein the removable portion is removable from the housing when the housing is mounted to the bicycle.

4. The device of claim 2, wherein the mounting member comprises one or more holes or slots passing through the housing and wherein the one or more holes or slots are spaced to match a bottle cage mounting location on a bicycle.

5. The device of claim 2, wherein the mounting member comprises one or more holes, slots, or grooves for receiving a zip tie for attachment to a frame of the bicycle.

6. The device of claim 1, wherein the watertight seal protects one or more of:
   electrical connectors for providing electrical communication between the removable portion and the housing; and
   a charging port on the removable portion for charging the battery.

7. The device of claim 1, wherein the watertight seal is formed between the housing and the removable portion at least in part by an elastomer material on one or more of the housing and the removable portion.

8. The device of claim 1, further comprising one or more of a microcontroller, a positioning system receiver, an accelerometer, a thermometer, a compass, and a barometer.

9. The device of claim 1, wherein the radio is configured to communicate the bicycle route information to a remote computing device comprising a portable computing device traveling with the bicycle.

10. The device of claim 1, wherein the radio is configured to communicate the bicycle route information to a remote computing device via a portable computing device traveling with the bicycle, wherein the portable computing device communicates the bicycle route information to a server or computing device over a wireless network.

11. A human powered transportation vehicle comprising:
   an activity tracker, the activity tracker comprising:
   a sensor component configured to obtain route information for the human powered transportation vehicle;
   a radio configured to wirelessly communicate the route information to a remote computing device;
   a housing comprising at least a portion of the sensor component and the radio, a coupling member that extends from the housing, and a coupling interface, wherein the coupling member includes one or more locking members for engaging and locking a removable portion, and wherein the coupling interface includes electrical contacts for connecting with a battery in the removable portion; and
   the removable portion comprising a battery, wherein the removable portion and the housing, when coupled, create a watertight seal between the removable portion and the housing to protect electronic components of the activity tracker.

12. The human powered transportation vehicle of claim 11, wherein the housing comprises a mounting member for securing the housing to the human powered transportation vehicle.

13. The human powered transportation vehicle of claim 12, wherein the removable portion is removable from the housing when the housing is mounted to the human powered transportation vehicle.

14. The human powered transportation vehicle of claim 12, wherein the mounting member comprises one or more holes or slots passing through the housing and wherein the one or more holes or slots are spaced to match one or more screw holes on a frame or other portion of the human powered transportation vehicle.

15. The human powered transportation vehicle of claim 12, wherein the mounting member comprises one or more holes, slots, or grooves for receiving a zip tie for attachment to a frame or other portion of the human powered transportation vehicle.

16. The human powered transportation vehicle of claim 11, wherein the watertight seal protects one or more of:
   electrical connectors for providing electrical communication between the removable portion and the housing; and
   a charging port on the removable portion for charging the battery.

17. The human powered transportation vehicle of claim 11, wherein the watertight seal is formed between the housing and the removable portion at least in part by an elastomer material on one or more of the housing and the removable portion.

18. The human powered transportation vehicle of claim 11, wherein the sensor component comprises one or more of a microcontroller, a positioning system receiver, an accelerometer, a thermometer, a compass, and a barometer.

19. The human powered transportation vehicle of claim 11, wherein the radio is configured to communicate the route information to a remote computing device comprising a portable computing device traveling with the human powered transportation vehicle or is configured to communicate the route information to a remote computing device via a portable computing device traveling with the human powered transportation vehicle, wherein the portable computing device communicates the route information to a server or computing device over a wireless network.

20. The human powered transportation vehicle of claim 11, wherein the coupling interface also includes a Universal Serial Bus (USB) port.

* * * * *